United States Patent [19]

Badmin et al.

[11] 4,374,833
[45] Feb. 22, 1983

[54] PYRETHROID PESTICIDAL COMPOSITION

[75] Inventors: John S. Badmin; Barry J. Mears, both of Sittingbourne, England

[73] Assignee: Shell Oil Company, Houston, Tex.

[21] Appl. No.: 286,508

[22] Filed: Jul. 24, 1981

[30] Foreign Application Priority Data

Aug. 20, 1980 [GB] United Kingdom ................ 8027082
Jan. 12, 1981 [GB] United Kingdom ................ 8100800

[51] Int. Cl.³ ...................... A01N 37/34; A01N 57/00
[52] U.S. Cl. ...................................... 424/225; 424/304
[58] Field of Search ................................ 424/225, 304

[56] References Cited

FOREIGN PATENT DOCUMENTS 13582 7/1980 European Pat. Off. .

OTHER PUBLICATIONS

Review of Applied Entomology Series A, 1980, vol. 68, No. 9, #4389.

Primary Examiner—Allen J. Robinson

[57] ABSTRACT

The invention provides pesticidal compositions containing the compound of formula I

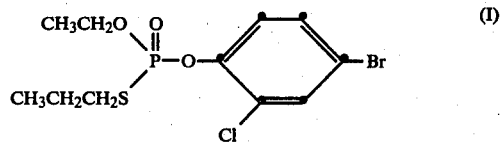

known as profenofos, and pyrethroid insecticides of formula

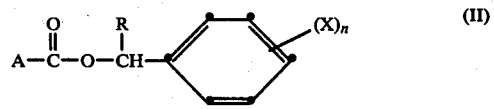

wherein A is an optionally-substituted aralkyl, alkyl, cycloalkyl or arylaminoalkyl group, R is hydrogen, cyano or ethynyl, X is alkyl, alkenyl, aralkyl or aryloxy and n is 1 to 5, and their use in combating pests, such as acarids.

1 Claim, No Drawings

PYRETHROID PESTICIDAL COMPOSITION

BACKGROUND OF THE INVENTION

1. Field of the Invention

The present invention relates to pesticidal compositions and their use.

2. Description of the Prior Art

O-(4-Bromo-2-chlorophenyl)-O-ethyl S-propyl phosphorothioate, commonly referred to as profenofos, is a known pesticide which may be prepared as described in British Pat. No. 1,417,116. On the other hand, a quite different class of insecticides is commonly referred to in the art as pyrethroid insecticides and these pyrethroids combine exceptional insecticidal properties with very low mammalian toxicity. For certain uses, an increase in the pesticidal spectrum of either kind of the above materials would be desirable.

SUMMARY OF THE INVENTION

It has now been discovered that mixtures of profenofos and certain pyrethroid insecticides exhibit surprising enhanced pesticidal activity against acarids, for example, *Tetranychus urticae*, the glasshouse red spider mite.

The invention provides a pesticidal composition which comprises:

(a) the compound of formula I

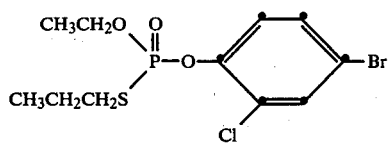

hereinafter referred to as profenofos; and (b) a pyrethroid insecticide of the formula II

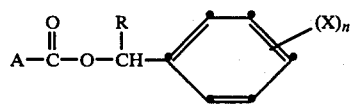

wherein A is an optionally-substituted aralkyl, alkyl, cycloalkyl or arylaminoalkyl group, R is hydrogen, cyano or ethynyl, X is alkyl, alkenyl, aralkyl or aryloxy and n is 1 to 5.

An alkyl, cycloalkyl or alkenyl group represented by A or X preferably contains up to 6 carbon atoms, and an aralkyl, arylaminoalkyl or aryloxy group represented by A or X preferably contains up to 12 carbon atoms.

It should be understood that the compound of the general formula II may be present in the form of any one of its optical or geometric, for example, cis-trans, isomers, or in the form of a mixture of isomers, for example, a racemate. A mixture of two or more compounds according to the general formula II may be present. The various isomers of the compounds according to formula II may have different insecticidal toxicities and/or knockdown potency. Thus, one may prefer to resolve mixtures of isomers to recover a more pesticidally active isomer or racemic mixture or to prepare the more active forms directly for use in the compositions of the invention.

When A represents an optionally-substituted cycloalkyl group, it preferably represents a cyclopropyl group of general formula:

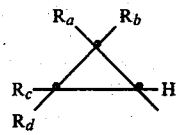

wherein $R_a$ and $R_b$ both represent an alkyl group having from 1 to 6 carbon atoms, especially a methyl group, or a halogen atom, especially a chlorine, bromine or fluorine atom; or $R_a$ and $R_b$ together represent an alkylene group having from 2 to 6, especially 3, carbon atoms; or $R_a$ represents a hydrogen atom and $R_b$ represents an alkenyl group having from 2 to 6 carbon atoms, especially an isobutenyl group, or a haloalkenyl group having from 2 to 6 carbon atoms and from 1 to 3 chlorine and/or bromine atoms, especially a monochlorovinyl, monobromovinyl, dichlorovinyl or dibromovinyl group, or a haloalkyl group having from 2 to 6 carbon atoms and from 2 to 5 chlorine and/or bromine atoms, especially a tetrachloroethyl, tetrabromoethyl or dibromodichloroethyl group; or $R_a$ and $R_b$ together with the interjacent carbon atom represent an unsaturated carbocyclic ring system of up to 12 carbon atoms, especially an indenylidene group; $R_c$ and $R_d$ both represent an alkyl group having 1 to 6 carbon atoms, especially a methyl group; or $R_c$ and $R_d$ together represent an alkylene group having from 2 to 6, especially 3, carbon atoms. Preferably, $R_a$ and $R_b$ both represent a methyl group or a chlorine atom, or $R_a$ and $R_b$ together represent an alkylene group containing 3 carbon atoms, or $R_a$ represents a hydrogen atom and $R_b$ represents an isobutenyl group, a monochlorovinyl, monobromovinyl, dichlorovinyl or dibromovinyl group or a tetrachloroethyl, tetrabromoethyl or dibromodichloroethyl group, or $R_a$ and $R_b$ together with the interjacent carbon atom represent an indenylidene group; and $R_c$ and $R_d$ both represent methyl groups or $R_c$ and $R_d$ together represent an alkylene group containing 3 carbon atoms.

When A in the general formula I represents an optionally-substituted aralkyl group, it preferably represents a substituted benzyl group of the general formula:

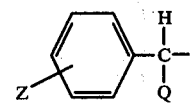

wherein Z represents a halogen, preferably chlorine, atom, or an alkoxy or haloalkoxy group of 1 to 4 carbon atoms, for example a methoxy or difluoromethoxy group, and Q represents an alkyl group of 1 to 6 carbon atoms, especially a branched chain group, for example an isopropyl group. Preferably the group Z is in the 4-position on the benzene ring.

When A represents an optionally substituted arylaminoalkyl group, it preferably represents a substituted anilinomethyl group of general formula:

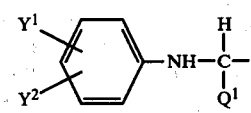

wherein $Y^1$ and $Y^2$ each independently represents a halogen, preferably chlorine, atom, or an alkyl or haloalkyl group of 1 to 4 carbon atoms, for example a trifluoromethyl group, and $Q^1$ represents an alkyl group of 1 to 6 carbon atoms, especially a branched chain group, for example an isopropyl group. Preferably $Y^1$ is a chlorine atom in the 2-position on the benzene ring and $Y^2$ is a trifluoromethyl group in the 4-position on the benzene ring.

Preferably n represents 1 and X represents a phenoxy or a benzyl group, especially a 3-phenoxy or 3-benzyl group.

The most preferred pyrethroid insecticides for use in the pesticidal composition according to the invention have the general formula II wherein A is alpha-isopropyl-4-chlorobenzyl, 2,2,3,3-tetramethylcyclopropyl, 2-(2,2-dichlorovinyl)-3,3-dimethylcyclopropyl; R is hydrogen or cyano; and n is 1 and X is 3-phenoxy. Especially preferred are the compounds known as cypermethrin, permethrin, decamethrin and fenvalerate whose formulae are given in the Examples herein.

The weight ratio of profenofos to the pyrethroid insecticide is preferably in the range of about 5:1 to about 1:300, more preferably in the range of about 1:1 to about 1:100.

The mixture of profenofos and the pyrethroid insecticides produces a surprising synergistic effect, for example, with respect to acarid pests, particularly mites, for example, *Tetranychus urticae*, the glasshouse red spider mite. The invention therefore also provides a method of combating pests at a locus which comprises applying to that locus a pesticidal composition according to the invention.

The pesticidal composition according to the invention preferably also comprises a carrier, especially at least two carriers, at least one of which is a surface-active agent.

This invention also provides a process for preparing a pesticidal composition which comprises bringing a compound of formula I and a pyrethroid insecticide of formula II into association with at least one carrier therefor.

A carrier in a composition according to the invention is any material with which the active ingredient is formulated to facilitate application to the locus to be treated, which may, for example, be a plant, seed or soil, or to facilitate storage, transport or handling. A carrier may be a solid or a liquid, including a material which is normally gaseous but which has been compressed to form a liquid, and any of the carriers normally used in formulating insecticidal or herbicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Pesticidal compositions are often formulated and transported in a concentrated form which is subsequently diluted by the user before application. The presence of small amounts of a carrier which is a surface-active agent facilitates this process of dilution.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary, co-solvent, 10–50% w/v active ingredient, 2–20% w/v emulsifiers and 0–20% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing insecticidal, herbicidal or fungicidal properties.

The following Examples illustrate the invention.

EXAMPLES 1 TO 4

Activity of pyrethroid/profenofos mixtures against *Tetranychus urticae*

(glasshouse red spider mite)

The acaricidal activities against *Tetranychus urticae* of profenofos, the pyrethroid insecticide of formula

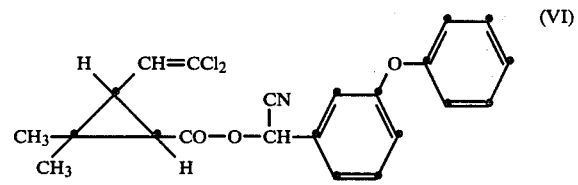

known as cypermethrin, the pyrethroid insecticide of formula

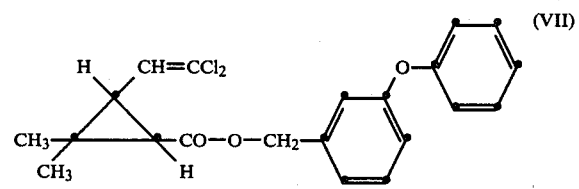

known as permethrin, the pyrethroid insecticide of formula

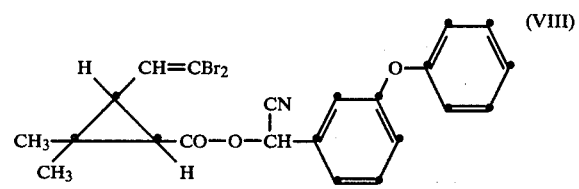

known as decamethrin, the pyrethroid insecticide of formula

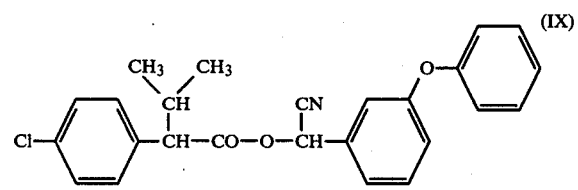

known as fenvalerate, and mixtures of profenofos with each of these four pyrethroid insecticides, were assessed by the following method.

The compounds and mixtures were formulated as solutions or suspensions in water containing 20% by weight of acetone and 0.05% by weight of Triton X-100 (Trade Mark) as wetting agent. The resulting compositions contained 0.4% by weight of the compound or mixture to be tested, and were subsequently diluted to produce compositions containing various concentrations. Leaf discs cut from french bean plants were sprayed with the compositions and left for ½ to 1 hour drying period. Each leaf disc was then innoculated with 10 red spider mites and mortality counts made 24 hours after innoculation. From these results the $LC_{50}$'s (the lethal concentration in weight percentage of active material in the compositions required to kill 50% of the mite population) were calculated.

Toxicity indices were then calculated using the following formula:

$$\text{Toxicity Index} = \frac{LC_{50} \text{ of standard}}{LC_{50} \text{ of compound or mixture}} \times 100$$

The standard used was ethyl parathion.

The joint action of the two active components of a mixture was analysed by the method of Yun-Pei Sun and E. R. Johnson, Journal of Economic Entomology, 1960, Vol. 53 no. 5, pp. 887–892. A coefficient of co-toxicity of a mixture is given by:

$$\text{coefficient of co-toxicity of mixture} = \frac{\text{actual toxicity index of mixture}}{\text{theoretical toxicity index of mixture}} \times 100$$

The theoretrical toxicity index of a mixture is equal to the sum over both components of the percentage of each individual compound present in the mixture multiplied by its respective toxicity index.

A coefficient of co-toxicity of a mixture near 100 indicates the probability of similar action by the two compounds; independent action usually gives a coefficient less than 100; and a coefficient significantly above 100 strongly indicates synergism.

The results obtained are illustrated in the following Table:

TABLE

| Example | Test Compounds | $LC_{50}$ | Coefficient of co-toxicity |
|---|---|---|---|
| | profenofos | 0.0029 | |
| | parathion | 0.0082 | |
| | cypermethrin | 0.29 | |
| | permethrin | 0.14 | |
| | decamethrin | 0.30 | |
| | fenvalerate | 0.21 | |
| 1 | profenofos/cypermethrin (1:80 mixture) | 0.039 | 306 |
| 2 | profenofos/permethrin (1:80 mixture) | 0.037 | 252 |
| 3 | profenofos/decamethrin (1:80 mixture) | 0.037 | 383 |
| 4 | profenofos/fenvalerate (1:80 mixture) | 0.046 | 224 |

The coefficients of co-toxicity obtained indicate synergism in the mixtures tested.

We claim:
1. A method of combating mites at a locus which comprises applying to the locus a miticidally effective amount of a composition comprising
(a) the compound of formula I

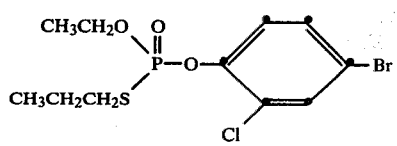
and
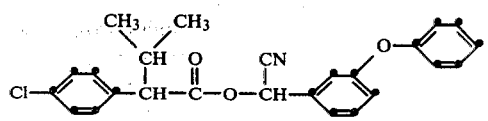
(b) the compound of formula II
in a ratio of (a) to (b) of 1:80.
* * * * *